United States Patent [19]

Martz et al.

[11] Patent Number: 5,080,656

[45] Date of Patent: Jan. 14, 1992

[54] TREATMENT OF DERMATOSES

[75] Inventors: Samuel J. Martz, Old Hickory; Myles D. Izikoff, Nashville, both of Tenn.

[73] Assignee: IHT, Inc., Nashville, Tenn.

[21] Appl. No.: 504,842

[22] Filed: Apr. 5, 1990

[51] Int. Cl.⁵ .................................. A61M 35/00
[52] U.S. Cl. ........................... 604/289; 606/131
[58] Field of Search ............... 128/898, 65–66; 604/22, 50, 56, 83, 85, 150, 289, 290; 606/131; 134/175; 132/272

[56] References Cited

U.S. PATENT DOCUMENTS

| | | | |
|---|---|---|---|
| 2,232,218 | 2/1941 | Doty | 128/65 |
| 3,521,647 | 7/1970 | Mercer | 132/272 |
| 4,670,010 | 6/1987 | Dragone | 604/289 |
| 4,834,121 | 5/1989 | Bell | 132/272 |

*Primary Examiner*—Stephen C. Pellegrino
*Assistant Examiner*—Glenn K. Dawson

[57] ABSTRACT

A process of treating papulosquamous disorders by the application of jet sprays. Impingement of the sprays under pressure results in a debriding action, removing scales from the skin.

4 Claims, No Drawings

TREATMENT OF DERMATOSES

BACKGROUND OF THE INVENTION

This invention relates to certain skin diseases or dermatoses. More particularly the invention relates to the treatment of that group of dermatoses, known as papulosquamous, and characterized by scales or plaques.

Papulosquamous diseases are a result of abnormal cell proliferation triggered by some type of biochemical stimulus. Skin injuries, emotional stress, and some forms of infections appear to trigger the development of such diseases. There also seems to be a hereditary factor involved. In these diseases, the skin cells form too rapidly to be eliminated. As a consequence of this abnormal keratin formation, papules either coalesce to form parakeratotic plaques, or they become overlain by dead cells. If the dead cells accumulate too rapidly to be removed, they also form these plaques, or scales. Papulosquamous diseases, which affect several million people, include psoriasis, pityriasis rosea, lichen planus, seborrheic dermatitis, and parapsoriasis.

Insofar as is known, no animal other than man has developed these diseases. Due to this lack of experimental animals, there are many unanswered questions about the causes and cures of papulosquamous diseases. What is known is that certain environmental factors can trigger the diseases.

Since causes of and cures for psoriasis and similar diseases are not well understood, efforts have had to be directed to treatment of the diseases rather than to their cures. Although research has been aimed at finding suitable topical therapy, or systemic treatments which exhibit minimal side effects, treatment of the diseases is still in its embryonic stages, directed mainly toward the removal of the plaques so medication can reach the proliferating cells. Current treatments, hence, have several drawbacks. Some have significant side effects; others are time consuming and messy; and all can be marginally effective with some people.

To aid in the removal of plaques or scales, they must first be softened. Two methods are most used, one taking about forty-five minutes, the other over twelve hours. As softening compositions, water can be used, but aqueous solutions are preferred, one such solution being a saline solution containing phenol. Oils and similar organic emollients are also employed, many still taking several hours to soften the plaques. To aid in the removal of scales, other oils or similar agents are then applied. The scales must then be physically removed by picking with a round- or fine-toothed comb or by brushing with a plastic shampoo brush. This practice is extremely painful to the patient. Moreover, if it is not done with care, or if the scales are not sufficiently softened, hair can be removed with the scales, and bleeding can occur. Once the scales are gone, medications are directly applied to the exposed skin or scalp. It can be seen that the removal of plaques formed by abnormal cell proliferation in papulosquamous diseases is a demoralizing, painful, and time consuming task which is subject to improvement. This invention is directed to an improved method of removing plaques. It is not time consuming; it is not painful; and it is relaxing.

SUMMARY OF THE INVENTION

There are many treatment regimes for patients with papulosquamous disorders, and many medications used. However, the medications are effective only after the scales are removed insofar as it is possible to do so. The parakeratotic plaques form barriers inhibiting the effects of topical medications. In the treatment for papulosquamous disorders herein, pressurized jet sprays are employed for plaque removal. Pressurized sprays reciprocatively impelled against the plaques introduce a relative movement between the jet spray and the plaques. By adjusting the pressure of the sprays based on the patient's tolerance, and on the thickness of the plaque layers, the reciprocative spray impingement results in a debriding action removing plaques from the skin. Once the bulk of the scales are gone, the medications or emollients can be applied directly to the skin, reaching affected areas.

DETAILED DESCRIPTION OF THE INVENTION

A machine reciprocatively impelling a spray under pressure on the head is the subject of U.S. Pat. No. 4,834,121. In that apparatus, manifolds travel back and forth along the head from the forehead to the neck. The manifolds are provided with nozzles so disposed that they direct jet spray on the head as the manifold reciprocatively moves. There is, then, relative motion between the jet spray and the head. It has been found that if the apparatus is provided with pressure adjustment means, such pressures, with this back-and-forth motion of the sprays, induce a saw-like action which loosens the plaques. Thus, if in the beginning, a low pressure, say close to 15 psi is introduced, and then increased, depending upon the thickness of the scales, up to the patient's toleration point, papulosquamos plaques are readily removed, the pressure range being 15 psi to 90 psi. In addition, the treatment period is correlated with the thickness of the plaques. The impingement of the spray on the parakeratotic plaques during this oscillatory movement of the manifold debrides the plaques. Concomitantly, shampoo can be injected through the jet sprays to wash away the scales, whereas other methods of plaque removal are extremely messy. Following the debridement of plaque particles or scales the scalp can be treated by sprays of medicinals known to be effective in the treatment of the particular papulosquamous disorder, or the medicine can be incorporated in the shampoo employed following plaque removal. Known medicinals for such diseases are liquid tar preparations, phenolics, salicylates, anthralin, salicylic acid, zinc pyrithione, some steroids, and some keratolytic agents known pressure regulating means are also available, and they are widely employed in hydraulic systems. One such pressure regulating system is described in co-filed patent application Ser. No. 07/504,844, now allowed.

SPECIFIC EXAMPLE

To experimentally determine efficacy of removing psoriasis plaques by spray at various pressures, tests were conducted by dermatology departments at eleven universities. It was found that by adjusting the pressure in relation to the patient's skin tolerance or sensitivity, no problems were encountered. Rather, if a lower pressure is required, the debriding action time is increased slightly. In the case of a 3+ scaling, at a high pressure, near 90 psi, the normal scale removal time is fourteen minutes. If the patient requires a lower pressure, say 60 psi, again for 3+ scaling, the plaque removal period is nineteen minutes. In addition, results obtained in both instances were superior to those obtained in the twelve hour method used heretofore. And in the prior art treatment methods, following the twelve hour softening period, it is was necessary to then remove the loosened scales with a scalp pick. Pressurized spray was found to reduce layers of scale to greater extent than known methods, rendering medication much more effective. It also eliminated the picking or combing operation. This is particularly important because that operation sometimes results in breaking the skin, breaking the hair off at the shaft, or in pulling hair out by the roots.

It can be seen then, that although no cure for psoriasis-type diseases exists, an adjunctive treatment for even severe cases is provided herein. In addition ramifications will occur to those skilled in the art. Thus, any of known medicines can be employed, and they can be incorporated in the softening solution, in the shampoo, or administered in a separate spray stage. Moreover, if desired, the medicine, if in the form of an ointment, can be applied by hand once the scales are removed by the practice of this process. Such modifications are deemed to be within the scope of this invention.

What is claimed is:

1. A process for treating papulosquamous disorders wherein papules have either coalesced to form plaques, or dead cells have accumulated to form plaques, and the resulting parkeratotic plaques form barriers inhibiting the effects of topical medications, the treatment comprising impelling pressurized liquid sprays against the plaques as reciprocating pressure sprays debriding the plaques, adjusting the pressure so that the sprays are impelled at a pressure of 15 psi, and the pressure is increased depending upon the thickness of the plaques and up to the toleration point of patient so that the reciprocative spray impingement maximizes the dibriding action, removing the plaques from the skin so that medications can reach the affected cells.

2. The process of claim 1 wherein the disorder is psoriasis.

3. A process for treating papulosquamous disorders wherein papules have either coalesced to form plaques, or dead cells have accumulated to form plaques, and the resulting parkeratotic plaques form barriers inhibiting the effects of topical medications, the treatment comprising impelling pressurized liquid sprays against the plaques as reciprocating pressure sprays debriding the plaques, adjusting the pressure so that the spray pressure is increased depending upon the thickness of the plaques and the toleration point of patient up to 90 psi so that the reciprocative spray impingement maximizes the dibriding action, removing the plaques from the skin so that medications can reach the affected cells.

4. The process of claim 3 wherein the disorder is psoriasis.

* * * * *